United States Patent [19]
Edwards

[11] Patent Number: 5,964,753
[45] Date of Patent: *Oct. 12, 1999

[54] INTEGRATED CARDIAC MAPPING AND ABLATION PROBE

[75] Inventor: Stuart D. Edwards, Los Altos, Calif.

[73] Assignee: EP Technologies, Inc., Sunnyvale, Calif.

[*] Notice: This patent is subject to a terminal disclaimer.

[21] Appl. No.: 09/003,087

[22] Filed: Jan. 5, 1998

Related U.S. Application Data

[63] Continuation of application No. 08/583,939, Jan. 4, 1996, Pat. No. 5,881,727, which is a continuation of application No. 08/136,648, Oct. 4, 1993, abandoned.

[51] Int. Cl.⁶ .............................. A61B 17/39; A61N 5/02
[52] U.S. Cl. .............................. 606/33; 606/41; 600/374; 607/101; 607/122; 607/156
[58] Field of Search ........................... 600/374; 606/41, 606/33; 607/122, 100–102, 156

[56] References Cited

U.S. PATENT DOCUMENTS

| | | |
|---|---|---|
| 4,522,212 | 6/1985 | Gelinas et al. . |
| 4,641,649 | 2/1987 | Walinsky et al. . |
| 4,660,571 | 4/1987 | Hess et al. . |
| 4,699,147 | 10/1987 | Chilson et al. . |
| 4,758,222 | 7/1988 | McCoy . |
| 4,785,815 | 11/1988 | Cohen . |
| 4,808,164 | 2/1989 | Hess . |
| 4,832,048 | 5/1989 | Cohen . |
| 4,892,102 | 1/1990 | Astrinsky . |
| 4,922,912 | 5/1990 | Watanabe . |
| 4,928,689 | 5/1990 | Hauser . |
| 4,940,064 | 7/1990 | Desai . |
| 4,955,382 | 9/1990 | Franz et al. . |
| 4,979,510 | 12/1990 | Franz et al. . |
| 4,998,916 | 3/1991 | Hammerslag et al. . |
| 5,010,894 | 4/1991 | Edhag . |
| 5,156,151 | 10/1992 | Imran . |
| 5,230,349 | 7/1993 | Langberg . |
| 5,237,996 | 8/1993 | Waldman et al. . |
| 5,242,441 | 9/1993 | Avitall . |
| 5,281,217 | 1/1994 | Edwards et al. ..................... 606/41 |
| 5,324,284 | 6/1994 | Imran . |
| 5,400,783 | 3/1995 | Pomeranz et al. . |
| 5,409,000 | 4/1995 | Imran . |
| 5,415,166 | 5/1995 | Imran . |
| 5,465,717 | 11/1995 | Imran . |
| 5,476,495 | 12/1995 | Kordis et al. . |

*Primary Examiner*—Lee Cohen
*Attorney, Agent, or Firm*—Lyon & Lyon LLP

[57] ABSTRACT

A probe for cardiac diagnosis and/or treatment has a catheter tube. The distal end of the catheter tube carries first and second electrode elements. The probe includes a mechanism for steering the first electrode element relative to the second electrode element so that the user can move the first electrode element into and out of contact with endocardial tissue without disturbing the contact of the second electrode element with endocardial tissue, even through the two electrode elements are carried on a common catheter tube. The distal end can carry a three dimensional structure having an open interior area. One of electrode elements can be steered through the open interior area of the structure. Electrode elements on the exterior of the structure can be used for surface mapping, while the electrode element inside the structure is steered to ablate tissue.

7 Claims, 6 Drawing Sheets

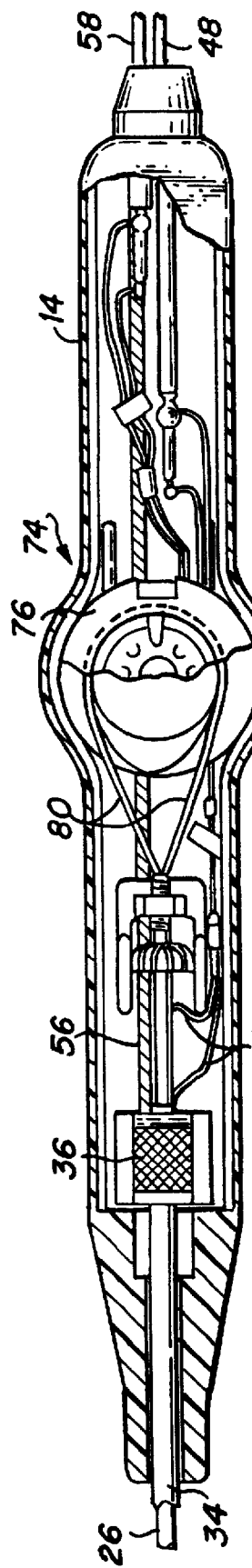
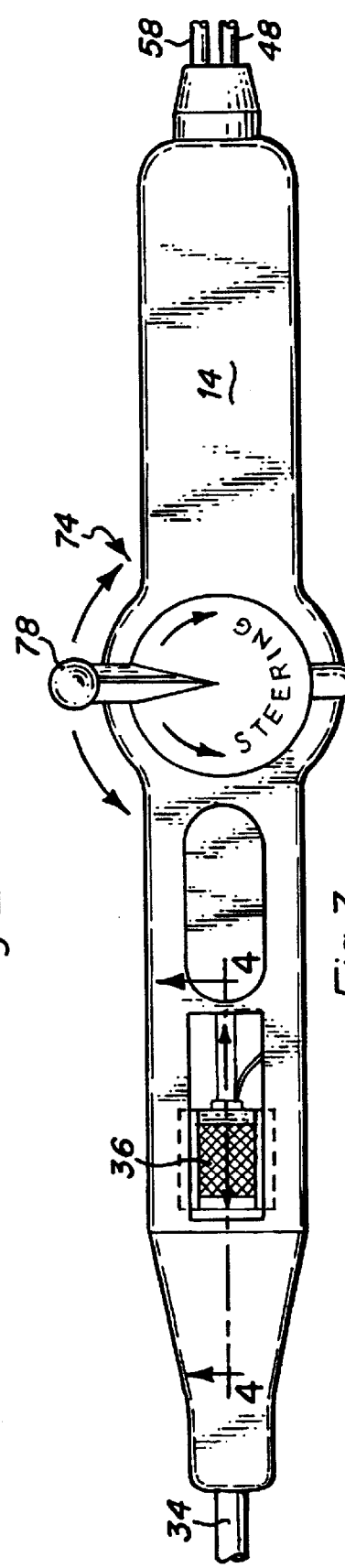
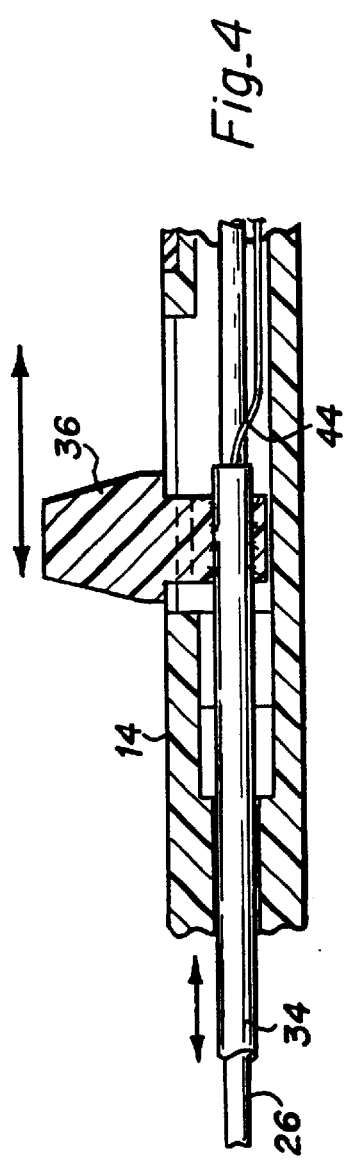

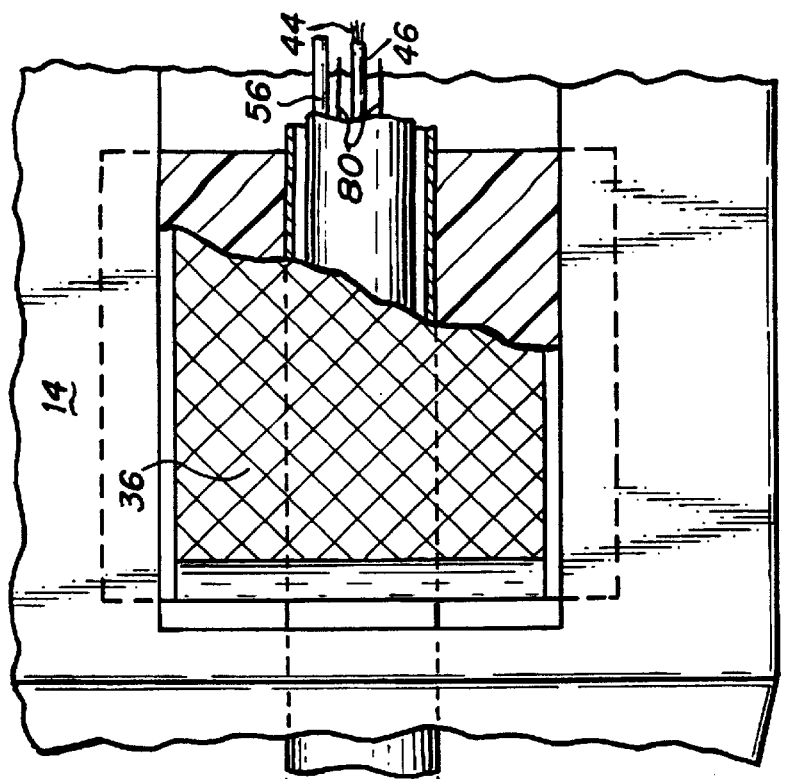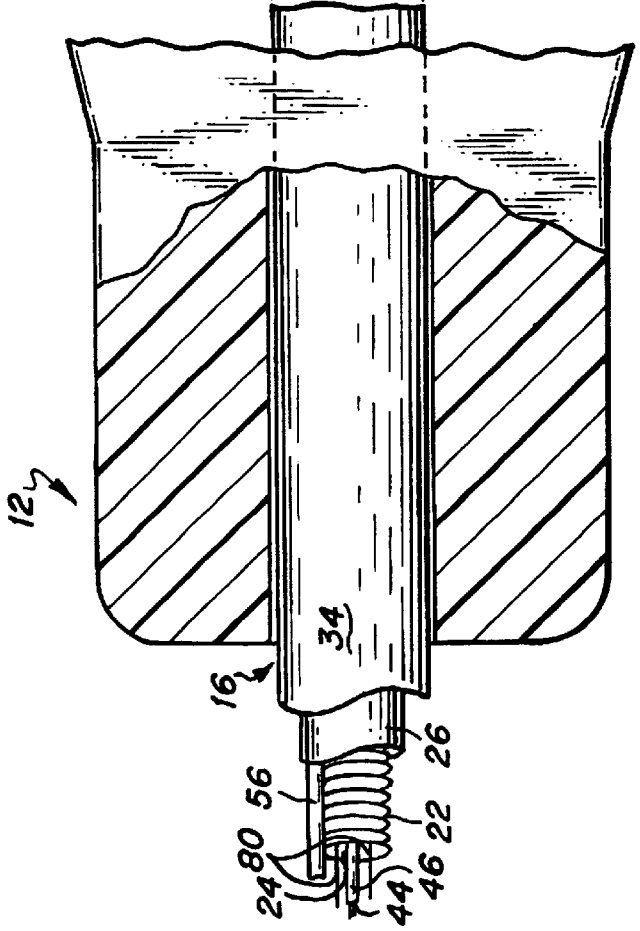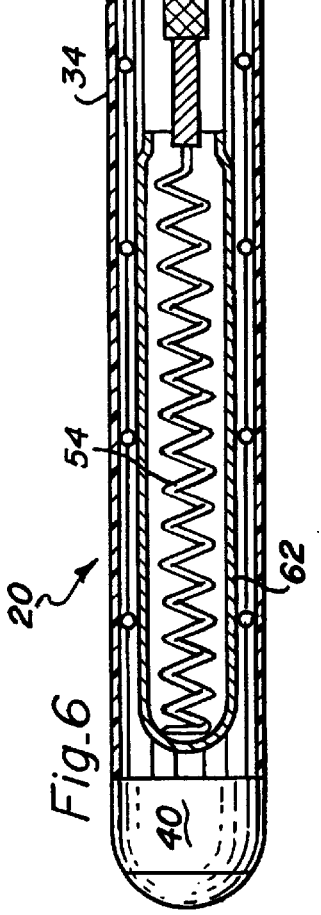

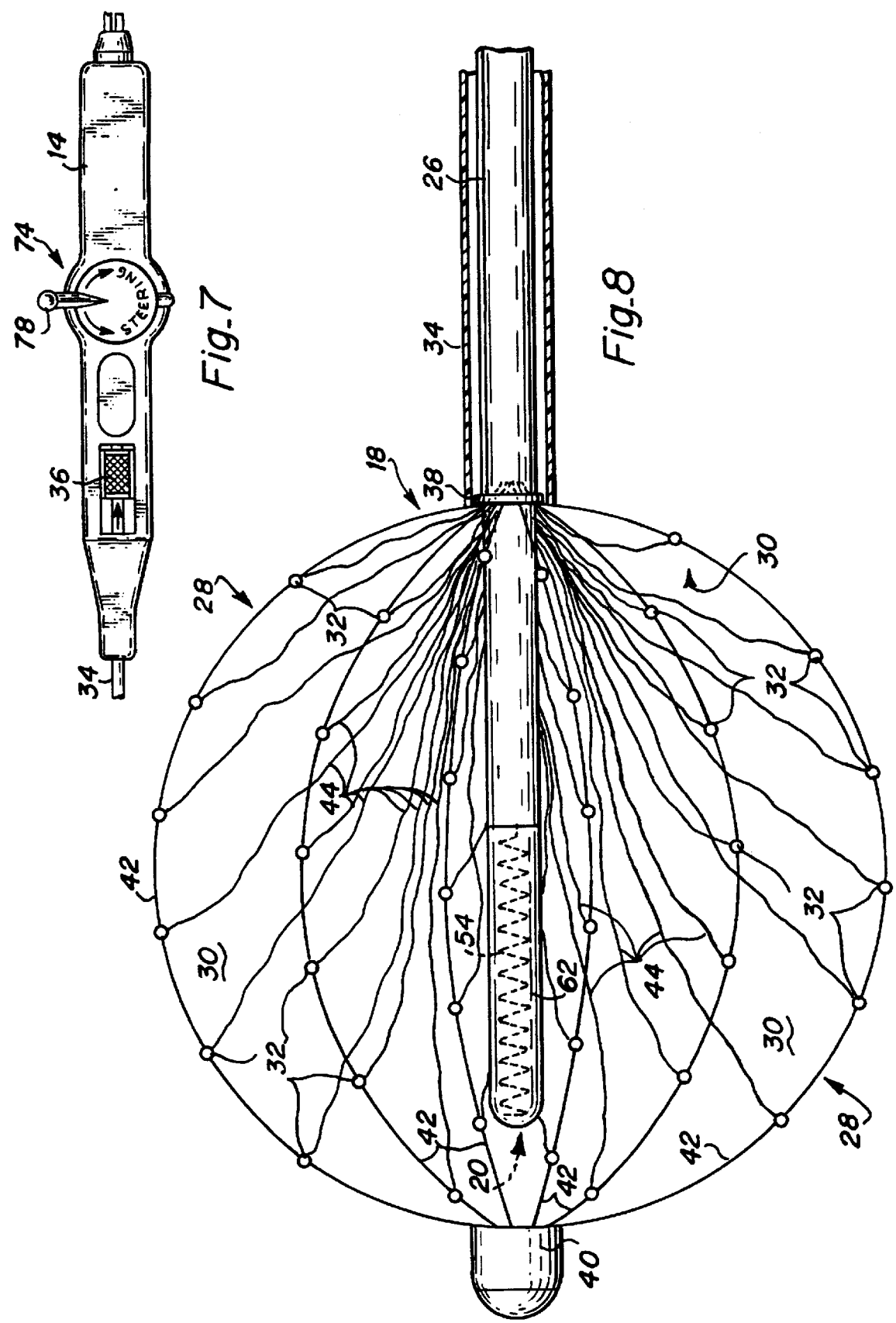

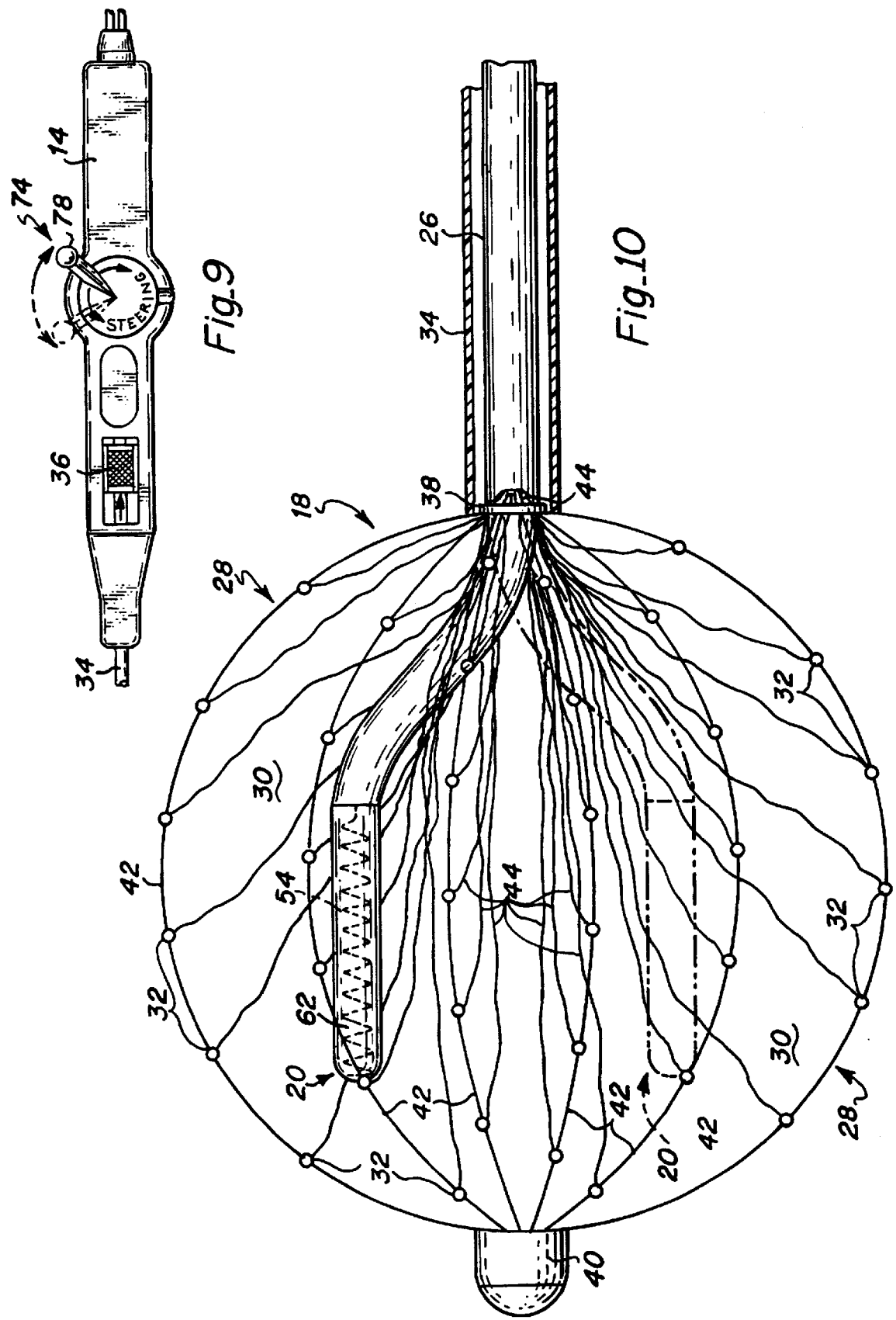

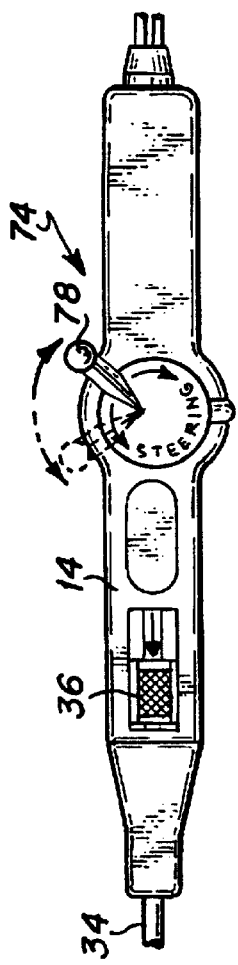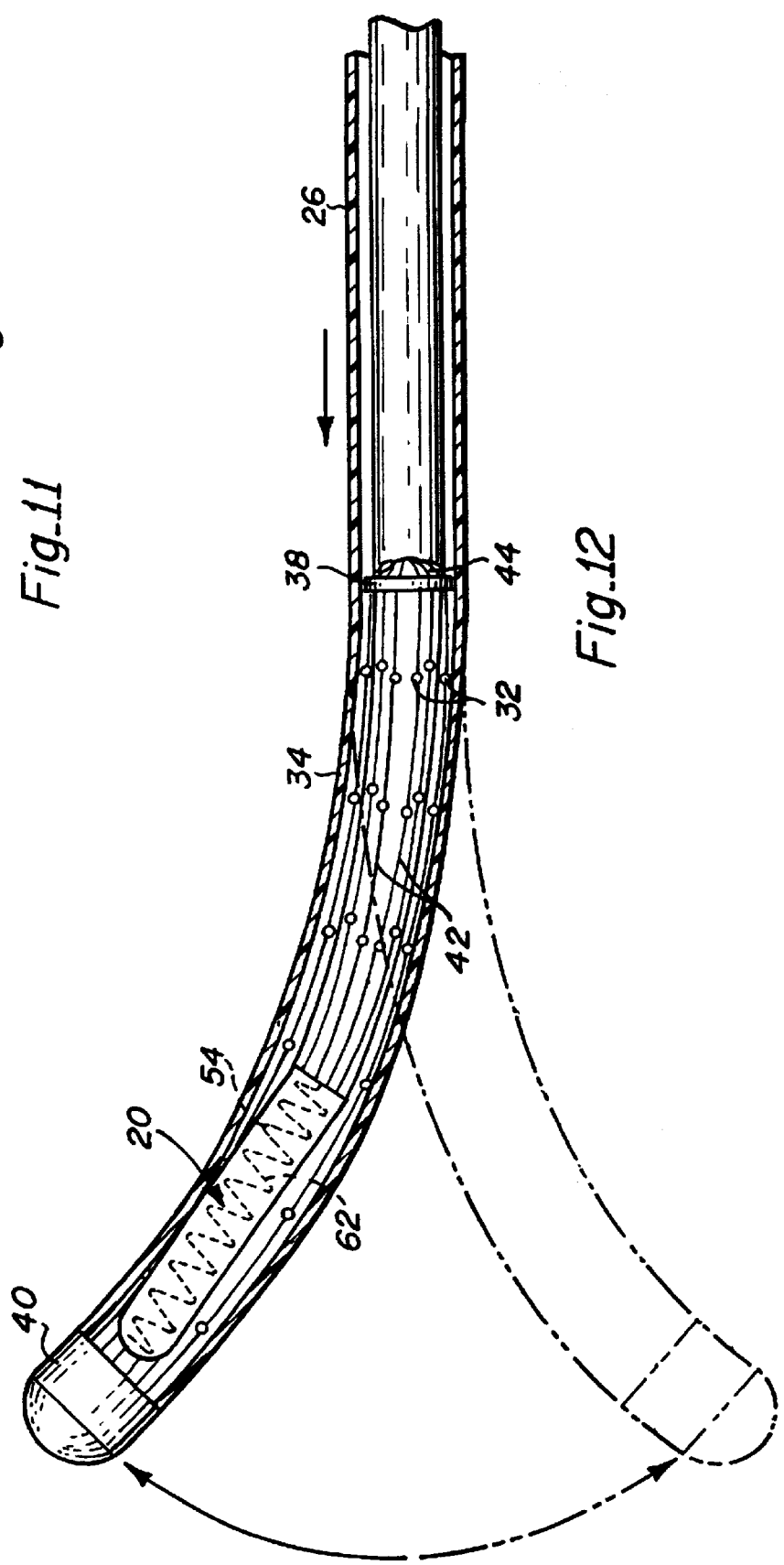

INTEGRATED CARDIAC MAPPING AND ABLATION PROBE

This a continuation of application Ser. No. 08/583,939, filed on Jan. 4, 1996, now U.S. Pat. No. 5,881,727, which is a continuation of application Ser. No. 08/136,648, filed on Oct. 14, 1993, now abandoned.

FIELD OF THE INVENTION

The invention relates to systems and methods for mapping and ablating the interior regions of the heart for treatment of cardiac conditions.

BACKGROUND OF THE INVENTION

Physicians make use of catheters today in medical procedures to gain access into interior regions of the body to ablate targeted tissue areas. It is important for the physician to be able to carefully and precisely control the position of the catheter and its emission of energy within the body during tissue ablation procedures.

The need for careful and precise control over the catheter is especially critical during procedures that ablate tissue within the heart. These procedures, called electrophysiological therapy, are becoming more widespread for treating cardiac rhythm disturbances.

During these procedures, a physician steers a catheter through a main vein or artery into the interior region of the heart that is to be treated. The physician then further manipulates a steering mechanism to place the electrode carried on the distal tip of the catheter into direct contact with the tissue that is to be ablated. The physician directs energy from the electrode through tissue to an indifferent electrode (in a uni-polar electrode arrangement) or to an adjacent electrode (in a bi-polar electrode arrangement) to ablate the tissue and form a lesion.

Cardiac mapping can be used before ablation to locate aberrant conductive pathways within the heart. The aberrant conductive pathways constitute peculiar and life threatening patterns, called dysrhythmias. Mapping identifies regions along these pathways, called foci, which are then ablated to treat the dysrhythmia.

There is a need for cardiac mapping and ablation systems and procedures that can be easily deployed with a minimum of manipulation and effort.

There is also a need for systems and procedures that are capable of performing cardiac mapping in tandem with cardiac ablation. Such multipurpose systems must also be easily introduced into the heart. Once deployed, such multipurpose systems also must be capable of mapping and ablating with a minimum of manipulation and effort.

SUMMARY OF THE INVENTION

A principal objective of the invention is to provide improved probes to carry out cardiac mapping and/or cardiac ablation procedures quickly and accurately.

Another principal objective of the invention is to provide improved probes that integrate mapping and ablation functions.

One aspect of the invention provides a probe having a catheter body. The distal end of the catheter body carries first and second operative elements. In use, the operative elements make contact with endocardial tissue independently of each other to perform therapeutic or diagnostic functions. According to this aspect of the invention, the probe includes a mechanism for steering the first operative element without altering the position of the second operative element.

According to this aspect of the invention, the user can move the first electrode element into and out of contact with endocardial tissue without disturbing the contact of the second electrode element with endocardial tissue, even though the two electrode elements are carried on a common catheter body. This aspect of the invention permits the first and second operative elements to perform the same or different functions.

For example, in a preferred embodiment, the first operative element serves to ablate myocardial tissue. The second operative element independently serves to sense electrical activity in endocardial tissue.

In this arrangement, the second operative element comprises one or more electrodes that map endocardial tissue to locate foci to be ablated. The first operative element can be steered to the foci located by the mapping electrodes, without interfering with their mapping function.

In one preferred embodiment, the second operative element can be operated to ablate myocardial tissue by thermal or chemical means, independently of the mapping function performed by the first electrode element.

In another aspect of the invention, the distal end of the catheter body carries a three dimensional structure having an open interior area. The structure has an exterior surface for contacting endocardial tissue. According to this aspect of the invention, the probe includes an operative element that extends from the distal end of the catheter body into the open interior area of the structure. The probe includes a mechanism for steering the operative element through the open interior area.

This aspect of the invention provides a three dimensional structure that surrounds the operative element to stabilize its position during use. The user can steer the operative element through the stabilizing structure to make selected contact with endocardial tissue.

In a preferred embodiment, the operative element ablates myocardial tissue. In this arrangement, the ablating element can take the form of an electrode that thermally destroys myocardial tissue. Alternatively, the ablating element can inject a chemical substance that destroys myocardial tissue.

In a preferred embodiment, the exterior surface of the structure carries electrode elements for sensing electrical activity in endocardial tissue. In this arrangement, the exterior electrode elements can be used to map the surface of endocardial tissue, while the interior element can be independently steered into position to ablate the tissue. This aspect of the invention provides a probe that integrates mapping and ablation functions.

Other features and advantages of the inventions are set forth in the following Description and Drawings, as well as in the appended claims.

BRIEF DESCRIPTION OF THE DRAWINGS

FIG. 2 is a plan view of the interior of the handle for the steerable catheter, partially broken away and in section, showing the mechanism for steering the distal tip of the catheter body;

FIG. 3 is a plan view showing the exterior of the handle of FIG. 2;

FIG. 4 is a fragmentary side cross sectional view of the handle of taken along Line 4—4 of FIG. 3;

FIG. 5 is a fragmentary sectional view on a greatly enlarged scale showing the mapping electrode deployment mechanism;

FIG. 6 is a plan view of an electrode-carrying basket and movable guide sheath shown in FIG. 1, with portions fragmented and in section, showing the electrode-carrying basket in a retracted condition;

FIG. 7 is a plan view of the handle showing the mapping basket control in the deployed position;

FIG. 8 is a view, partially broken away and in section, showing the guide sheath and the steerable catheter body advanced into the deployment position;

FIG. 9 is a plan view of the handle showing the mapping basket control in the deployed position illustrating use of the steering control mechanism to steer the ablation catheter;

FIG. 10 is a view, partially broken away and in section, showing the guide sheath and the steerable catheter body advanced into the deployment position with the ablation electrode steered into position for use;

FIG. 11 is a plan view of the handle illustrating steering of the probe with the electrode-carrying basket retracted; and, FIG. 12 is an enlarged plan view of probe distal tip illustrating steering of the probe with the electrode-carrying basket retracted.

DESCRIPTION OF THE PREFERRED EMBODIMENTS

Figure 1:
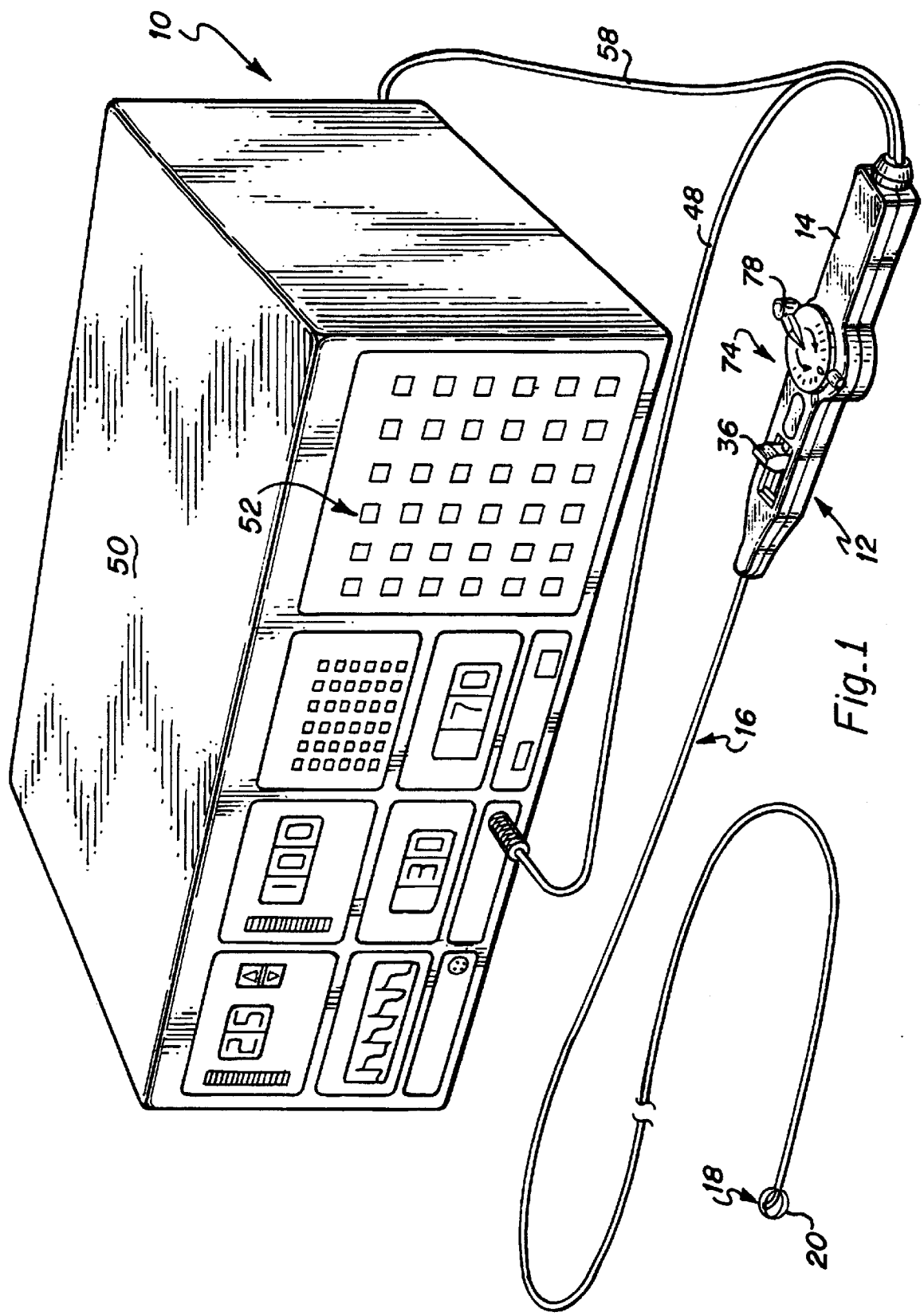
FIG. 1 is a perspective view of a probe and monitoring system that embodies the features of the invention.

FIG. 1 shows an endocardial mapping system 10 that embodies features of the invention.

The system 10 includes a catheter probe 12.

The catheter probe 12 includes a handle 14, to which a flexible guide body 16 is attached.

The distal end of the guide body 16 carries a three dimensional structure 18. The structure 18 takes the form of a basket, as best shown in FIGS. 8 and 10.

The three dimensional basket structure 18 includes an exterior surface 28 that encloses an open interior area 30. The basket structure 18 carries a three dimensional array of electrodes 32 on its exterior surface 28. When deployed inside the heart chamber, the exterior surface 28 of the basket structure 18 holds the electrodes 32 against the endocardial surface.

According to the invention, the three dimensional structure 18 carries within it a steerable ablating element 20. The ablating element 20 is moveable through the interior area 20 without requiring movement of the structure 18 itself.

As FIG. 5 best shows, the guide body 16 comprises a multi-layer tubular construction. It includes at its core a length of stainless steel coiled into a flexible spring 22 enclosing an interior bore 24. A braided sheath 26 of plastic material surrounds the guide spring 22.

As FIG. 5 also shows, the guide body 16 also includes an outer sheath 34 that surrounds the inner sheath 26. The outer sheath 34 is made from an inert plastic material, which, in the preferred embodiment, comprises a nylon composite material. The sheath 34 has an inner diameter that is greater than the outer diameter of the inner sheath 26. As a result, the outer sheath 34 can slide along the inner sheath 26.

The handle 14 carries a control knob 36, which is attached to the sheath 16 (see FIGS. 2 to 4). Forward movement of a control knob 36 (see FIG. 11) advances the distal end of the slidable sheath 34 upon the basket structure 18. The slidable sheath 34 captures and collapses the basket structure 18 (as FIGS. 6 and 12 show). In this position, the distal end of the sheath 34 entirely encloses the basket structure 18. The physician introduces the basket structure 18 into the selected heart chamber through a selected vein or artery when in this collapsed, low profile condition.

Rearward movement of the control knob 36 (see FIGS. 7 and 8) retracts the slidable sheath 34 away from the basket structure 18. The basket structure 18 opens to assume its prescribed three dimensional shape, as FIG. 8 shows. The basket structure 18 is thereby deployed for use within the heart chamber.

The basket 18 can be variously constructed. In the illustrated and preferred embodiment (best shown by FIGS. 9 and 11), the basket 24 comprises an annular base member 38 attached about the inner sheath 26. The basket 24 also includes an end cap 34.

Generally flexible splines 42 extend in a circumferentially spaced relationship between the base member 38 and the end cap 40. In the illustrated embodiment, six splines 42 form the basket 18. However, additional or fewer splines 42 could be used, depending upon the application.

In this arrangement, the splines 42 are made of a resilient inert material, like Nitinol metal or silicone rubber. The splines 42 are connected between the base member 38 and the end cap 40 in a resilient, pretensed condition, as shown in FIG. 10. In this configuration, the resilient splines 42 bend and conform to the tissue surface they contact.

As FIGS. 6 and 12 show, the splines 42 also collapse into a closed, compact bundle in response to an external compression force, which the external sheath 34 provides.

In the illustrated embodiment (as FIG. 8 shows), each spline 42 carries six electrodes 32. Of course, additional or fewer electrodes 32 can be used. In the preferred embodiment, the electrodes 32 are made of platinum or gold plated stainless steel.

Signal wires 44 made from a highly conductive metal, like copper, lead from the electrodes 32. The signal wires 44 extend down the associated spline 42, through the base member 38, and into the bore 24 of the guide spring 22 (see FIGS. 5 and 6). An inert plastic electrically insulating sheath preferably covers each spline 42 to also enclose the signal wires 44. In the preferred embodiment, the sheath is made of a polyurethane elastomer.

The six signal wires 44 for each spline 42 are twisted together to form a common bundle 46 (see FIGS. 5 and 6). As FIGS. 5 and 6 show, the common bundle 46 is, in turn, passed through the bore 24 of the guide spring 22 and into the probe handle 14 (see FIG. 2).

The thirty six signal wires 44 attach via a signal cable to an external controller 50, as FIG. 1 shows.

When deployed, the electrodes 32 record the electrical potentials in myocardial tissue. The controller 50 derives the activation times, the distribution, and the waveforms of the potentials recorded by the basket electrodes 32. As FIG. 1 shows, displays 52 can be provided to indicate electrical potential measurements at each electrode 32.

In an alternative arrangement, ablating energy can be applied through a selected one or more of the basket electrodes 32.

In the illustrated and preferred embodiment, the movable ablating element 20 is an integral part of the probe 18. The type of ablating energy used can vary. The physician can ablate tissue by using an electrode to thermally destroy myocardial tissue, either by heating or cooling the tissue. Alternatively, the physician can inject a chemical substance that destroys myocardial tissue. The physician can use other means for destroying myocardial tissue as well.

In the illustrated embodiment, the ablating element 20 takes the form a coaxial antenna assembly that emits electromagnetic microwave energy. The ablating antenna assembly 20 extends beyond the distal end of the guide spring 22 and its associated inner sheath 26.

The details of the microwave antenna assembly 20 and its attachment to the guide spring 22 are shown in copending application Ser. No. 07/868,031, filed Apr. 13, 1992, entitled "Steerable Antenna Systems for Cardiac Ablation that Minimize Tissue Damage and Blood Coagulation Due to Conductive Heating Patterns," which is incorporated herein by reference.

The ablating antenna assembly 20 includes an antenna 54 (see FIG. 6). The antenna 54 forms a helix with about 10 turns. Based upon its size and helical pattern, the operating frequencies of the antenna 54 is either about 915 MHz or 2450 Mhz.

The antenna assembly 20 includes an associated coaxial cable 56. The cable 56 extends from within the handle 14 (see FIG. 2) along the outside of the guide spring 22 and within the sheath 32 (see FIG. 5). A supply cable 58 (see FIGS. 1 and 2) is joined to the proximal end of the antenna cable 56. The supply cable 58 conducts microwave ablating energy from the controller 50 to the antenna 54 for propagation at the lesion site.

The ablating antenna assembly 20 includes its own steering assembly 74. The steering mechanism 74 for the ablating antenna assembly 20 may vary. In the illustrated embodiment, the steering mechanism 74 is of the type shown in copending application Ser. No. 07/868,031, which is identified above and which is also incorporated herein by reference.

In the illustrated embodiment (see FIG. 2), the steering mechanism 74 includes an interior cam wheel 76 located within the handle 14. An external steering lever 78 (see FIG. 3) rotates the cam wheel 76. The cam wheel 76 holds the proximal ends of right and left steering wires 80.

As FIG. 2 shows, steering wires 80 extend from the associated left and right side surfaces of the cam wheel 76. The steering wires 80 extend through the bore 24 guide spring 22 (see FIG. 5) to the ablating antenna assembly 20.

The steering wires 80 attach to opposite sides to a steering spring 60 (see FIG. 6). The steering spring 60 is, in turn, soldered to the distal end of the antenna cable 56.

The helix antenna 54 extends distally from this juncture, being enclosed within a shroud 62 of potting compound. The potting compound shroud 62 preferable includes a particles of diamond or sapphire that provide a high dielectric constant; low microwave energy loss; and high thermal conductivity.

When the ablation element 20 is deployed out of the sheath 34 (as FIGS. 9 and 10 show), forward movement of the steering lever 78 bends the ablation element 20 down (as shown in phantom lines) while rearward movement bends the ablation element 20 up (as shown in solid lines). The element 20 moves through the basket 18 between a generally straight configuration (as FIG. 8 shows) and the up and down deflected positions (as FIGS. 9 and 10 show), to selectively place the ablating element 20 in contact with endocardial tissue.

By manipulating the steering lever 78, the physician can maneuver the ablating element 20 under fluoroscopic control through the basket 18 into contact with any point of the endocardial surface of the chamber. The ablating element 20 can be moved through the basket 18 to tissue locations either in contact with the exterior surface of the basket 18 or laying outside the reach of the basket 18 itself. Ablating energy can then be applied to thermally destroy the tissue.

Furthermore, as FIGS. 11 and 12 show, by manipulating the steering lever 78 when the outer sheath 34 is moved forward, the physician can maneuver or steer the entire distal tip of the probe 18 during its introduction into the selected heart chamber.

Various features of the invention are set forth in the following claims.

What is claimed is:

1. A probe for use within a living body, comprising a catheter tube having a distal end;

a three dimensional structure on the distal end having an open interior area, the structure having an exterior surface for contacting tissue within the living body;

a steerable support body carrying at least one ablating element and extending from the distal end of the catheter tube into the open interior area of the structure, the steerable support body and the three dimensional structure both being integral with the catheter tube; and a mechanism to steer the steerable support body within the open interior area.

2. A probe according to claim 1, wherein the at least one ablating element emits electromagnetic microwave energy.

3. A probe according to claim 1, wherein the at least one ablating element includes an antenna.

4. A probe according to claim 3, wherein the antenna forms a helix with about 10 turns.

5. A probe according to claim 3, wherein the operating frequency of the antenna is either approximately 915 MHZ or approximately 2450 MHZ.

6. A probe according to claim 3, wherein the antenna is enclosed within a shroud of potting compound.

7. A probe according to claim 6, wherein the potting compound shroud comprises a material made of a high dielectric constant, low microwave energy loss, and high thermal conductivity.

* * * * *